(12) United States Patent
Schmidt et al.

(10) Patent No.: US 7,270,881 B2
(45) Date of Patent: Sep. 18, 2007

(54) COATED WATER-SWELLABLE MATERIAL

(75) Inventors: Mattias Schmidt, Idstein (DE); Axel Meyer, Frankfurt am Main (DE); Bruno Johannes Ehrnsperger, Mason, OH (US); Stephen Allen Goldman, Montgomery, OH (US); Edward Joseph Urankar, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 14 days.

(21) Appl. No.: 10/912,002

(22) Filed: Aug. 5, 2004

(65) Prior Publication Data

US 2005/0043696 A1    Feb. 24, 2005

Related U.S. Application Data

(60) Provisional application No. 60/492,932, filed on Aug. 6, 2003.

(51) Int. Cl.
    *B32B 5/16*    (2006.01)
(52) U.S. Cl. .................................... 428/407; 428/423.1
(58) Field of Classification Search ................ 428/403, 428/407, 423.1
    See application file for complete search history.

(56) References Cited

U.S. PATENT DOCUMENTS

| | | |
|---|---|---|
| 4,062,817 A | 12/1977 | Westerman |
| 4,093,776 A | 6/1978 | Aoki et al. |
| 4,156,664 A | 5/1979 | Skinner et al. |
| 4,392,908 A | 7/1983 | Dehnel |
| 4,541,871 A | 9/1985 | Obayashi et al. |
| 4,625,001 A | 11/1986 | Tsubakimoto et al. |
| 4,666,983 A | 5/1987 | Tsubakimoto et al. |
| 4,734,445 A | 3/1988 | Noda et al. |
| RE32,649 E | 4/1988 | Brandt et al. |
| 4,824,901 A | 4/1989 | Alexander et al. |
| 4,835,211 A | 5/1989 | Noda et al. |
| 5,140,076 A | 8/1992 | Hatsuda et al. |
| 5,164,459 A | 11/1992 | Kimura et al. |
| 5,378,528 A * | 1/1995 | Makoui ...................... 428/219 |
| 5,470,964 A | 11/1995 | Qin |
| 5,562,646 A | 10/1996 | Goldman et al. |
| 5,633,316 A | 5/1997 | Gartner et al. |
| 5,714,156 A | 2/1998 | Schmidt et al. |
| 5,731,365 A | 3/1998 | Engelhardt et al. |
| 5,840,329 A | 11/1998 | Bai |
| 5,849,816 A | 12/1998 | Suskind et al. |
| 5,851,672 A | 12/1998 | Wang et al. |
| 5,976,696 A * | 11/1999 | Collette et al. ............. 428/407 |
| 6,140,550 A * | 10/2000 | Beihoffer et al. ........... 604/366 |
| 6,150,469 A | 11/2000 | Harada et al. |
| 6,239,230 B1 | 5/2001 | Eckert et al. |
| 6,353,148 B1 * | 3/2002 | Gross .......................... 604/368 |
| 6,376,011 B1 | 4/2002 | Reeves et al. |
| 6,387,495 B1 | 5/2002 | Reeves et al. |
| 6,391,451 B1 | 5/2002 | Mitchell et al. |
| 6,534,572 B1 | 3/2003 | Ahmed et al. |
| 7,049,000 B2 * | 5/2006 | Fossum et al. ............. 428/402 |
| 7,173,086 B2 * | 2/2007 | Smith et al. ................. 524/556 |
| 2002/0128618 A1 | 9/2002 | Frenz et al. |

FOREIGN PATENT DOCUMENTS

| | | |
|---|---|---|
| EP | 0 799 258 B1 | 10/1997 |
| JP | 56 159232 A | 12/1981 |
| WO | WO90/08789 A1 | 8/1990 |
| WO | WO92/16565 A1 | 10/1992 |
| WO | WO93/05080 A1 | 3/1993 |
| WO | WO96/14885 A1 | 5/1996 |
| WO | WO 03/043670 A1 | 5/2003 |

* cited by examiner

*Primary Examiner*—H. Thi Le
(74) *Attorney, Agent, or Firm*—John G. Powell; Eric T. Addington; Edward J. Milbrada

(57) ABSTRACT

This invention is directed to coated water-swellable materials, typically solid, particulate, water-swellable materials, i.e. materials that comprise hydrogel-forming polymers, whereof at least a part is coated with a coating, which substantially does not break when the polymers swell, as set out in the method herein. Said coating is present at a level of at least 1% by weight of the water-swellable material.

The coating comprises preferably an elastomeric polymeric material. The invention also relates products, e.g., disposable absorbent articles, comprising such coated water-swellable material.

11 Claims, No Drawings

COATED WATER-SWELLABLE MATERIAL

CROSS REFERENCE TO RELATED APPLICATIONS

This application claims the benefit of U.S. Provisional Application No. 60/492,932, filed Aug. 6, 2003.

FIELD OF THE INVENTION

This invention is directed to coated water-swellable materials, typically solid, particulate, water-swellable materials, i.e., materials that comprise hydrogel-forming polymers, whereof at least a part is coated with a coating agent with a polymeric elastomeric material, which substantially does not rupture when the polymers swell, as set out in the method herein.

The coating agent comprises preferably an elastomeric polymeric material. The invention also relates products, e.g., disposable absorbent articles, comprising such coated water-swellable material.

BACKGROUND OF THE INVENTION

An important component of disposable absorbent articles such as diapers is an absorbent core structure comprising water-swellable polymers, typically hydrogel-forming water-swellable polymers, also referred to as absorbent gelling material, AGM, or super-absorbent polymers, or SAP's. This polymer material ensures that large amounts of bodily fluids, e.g., urine, can be absorbed by the article during its use and locked away, thus providing low rewet and good skin dryness.

Especially useful water-swellable polymer material or SAP's are often made by initially polymerizing unsaturated carboxylic acids or derivatives thereof, such as acrylic acid, alkali metal (e.g., sodium and/or potassium) or ammonium salts of acrylic acid, alkyl acrylates, and the like in the presence of relatively small amounts of di- or poly-functional monomers such as N,N'-methylenebisacrylamide, trimethylolpropane triacrylate, ethylene glycol di(meth)acrylate, or triallylamine. The di- or poly-functional monomer materials serve to lightly cross-link the polymer chains thereby rendering them water-insoluble, yet water-swellable. These lightly crosslinked absorbent polymers contain a multiplicity of carboxyl groups attached to the polymer backbone. It is generally believed, that these carboxyl groups generate a driving force for the absorption of body fluids by the crosslinked polymer network.

In addition, the polymer particles are often treated as to form a surface cross-linking 'coating' on the outer surface in order to improve their properties in particular for application in baby diapers.

Water-swellable (hydrogel-forming) polymers useful as absorbents in absorbent members and articles such as disposable diapers need to have adequately high sorption capacity, as well as adequately high gel strength. Sorption capacity needs to be sufficiently high to enable the absorbent polymer to absorb significant amounts of the aqueous body fluids encountered during use of the absorbent article. Together with other properties of the gel, gel strength relates to the tendency of the swollen polymer particles to deform under an applied stress, and the gel strength needs to be high enough so that the particles do not deform and fill the capillary void spaces in the absorbent member or article to an unacceptable degree, so-called gel blocking. This gel-blocking inhibits the rate of fluid uptake or the fluid distribution, i.e. once gel-blocking occurs, it can substantially impede the distribution of fluids to relatively dry zones or regions in the absorbent article and leakage from the absorbent article can take place well before the water-swellable polymer particles are fully saturated or before the fluid can diffuse or wick past the "blocking" particles into the rest of the absorbent article. Thus, it is important that the water-swellable polymers (when incorporated in an absorbent structure or article) maintain a high wet-porosity and have a high resistance against deformation thus yielding high permeability for fluid transport through the swollen gel bed.

Absorbent polymers with relatively high permeability can be made by increasing the level of internal crosslinking or surface crosslinking, which increases the resistance of the swollen gel against deformation by an external pressure such as the pressure caused by the wearer, but this typically also reduces the absorbent capacity of the gel undesirably.

The inventors found that often the surface crosslinked water-swellable polymer particles are constrained by the surface-crosslinking 'shell' and cannot absorb and swell sufficiently, and/or that the shell is not strong enough to withstand the stresses of swelling or the stresses associated with performance under load.

The inventors have found that the coatings or shells of the water-swellable polymers, as used in the art, including surface cross-linking 'coatings', break when the polymer swells significantly or that the 'coatings' break after having been in a swollen state for a period of time. They also found that, as a result thereof, the coated and/or surface-crosslinked water-swellable polymers or super-absorbent material known in the art de-form significantly in use thus leading to relatively low porosity and permeability of the gel bed in the wet state. They found that this could be detrimental to the optimum absorbency, liquid distribution or storage performance of such polymer materials.

Thus, the inventors found that what is required are water-swellable materials comprising coated water swellable polymers that have a coating that can exert a force in the wet state and that does substantially not rupture when the polymers swell in body liquid under typical in-use conditions. In the context of this invention, the inventors have found that as a good representative for body liquids such as urine, a 0.9% sodium chloride by weight in water solution, further called "0.9% saline" can be used. Therefore the inventors have found that it is required to have coated water swellable materials, or coated hydrogel forming polymers, where the coating does substantially not rupture when the materials swell in 0.9% saline.

The inventors have now developed a new water-swellable material comprising hydrogel forming polymers, of which at least a part is coated with a coating agent, which is elastomeric, so that when the internal core of material swells (and forms a hydrogel), the coating can extend and remains substantially intact, i.e., without breaking.

The inventors further found improved or preferred processes of applying and subsequently treating the coatings, as to obtain preferred material of the present invention, with further improved properties.

SUMMARY OF THE INVENTION

The present invention relates to water-swellable material that comprises hydrogel-forming polymers coated by a coating, formed from a coating agent comprising an elastomeric polymeric material, whereby said coating is present at a level of at least 1% by weight of the water-swellable material, and whereby the water swellable material has a CCRC of at least 10 g/g (or even at least 20 g/g or even at least 30 g/g) and whereby, for at least a part of the coated hydrogel forming polymers, said coating is non-breaking, when the water-swellable material is swollen to equilibrium in 0.9% saline solution by the method defined herein.

Said part of the coated hydrogel forming polymers that has a non-breaking coating of an elastomeric polymeric material is at least 60% by weight, or even at least 80% or even at least 90% or even at least 95% or even 100% by weight of the material, having a coating with an elastomeric, polymeric material.

The coating agent is applied such that the resulting coating layer is preferably thin; preferably the coating layer has an average caliper (thickness) between 1 micron to 200 microns (μm), more preferably from 1 micron to 100 microns or even to 50 microns or even to 20 microns, or even more preferably from 2 to 15 microns.

The water-swellable material and the hydrogel forming polymers are preferably solid, preferably particulate.

The coating agent comprises preferably natural or synthetic elastomeric polymeric materials, preferably elastomeric polymeric materials selected from the group of natural rubber, synthetic rubber and thermoplastic elastomers that are elastic at 35° C.

The inventions also relates to absorbent structures, suitable for (disposable) absorbent articles, comprising the water-swellable material of the invention, and to such absorbent articles, such as diapers.

The intention also relates to a process for making the water-swellable material of the invention by the steps:
  a) obtaining hydrogel forming polymers; and
  b) simultaneously with or subsequently to step a), applying a coating agent, comprising an elastomeric material, to at least part of said hydrogel forming polymers to obtain coated hydrogel forming polymers; and preferably
  c) prior to, simultaneous with or subsequent to step b), obtaining said hydrogel forming polymers or coated hydrogel forming polymers in solid, preferably particulate, form.

The process preferably comprises a curing step, to cure the coatings, e.g., preferably subsequently or simultaneously with step c), the coated polymers are subjected to a temperature of at least 80° Celsius, preferably at least 100° Celsius, more preferably at least about 140° Celsius.

The invention also relates to the use of the process above to increase the porosity of the hydrogel-forming polymers in the wet state.

DETAILED DESCRIPTION

Water-swellable Material, Hydrogel Forming Polymers and Resulting Coatings

The water-swellable material of the invention is such that it swells in water by absorbing the water, thereby forming a hydrogel. It may also absorb other liquids and swell. Thus, when used herein, 'water-swellable' means that the material swells at least in water, but typically also in other liquids or solutions, preferably in water based liquids such as 0.9% saline.

The water-swellable material of the invention comprises at least 60% by weight (of the material) of hydrogel forming polymers that are coated with an elastomeric, polymeric coating agent that forms a non-breaking coating.

This can be determined by observation of the coating of the material of the invention, by any known method for observing the surface structure or coating of solid materials, such as with the methods described below.

Hereby, a certain weight amount of the water-swellable material is stained and swollen to its equilibrium (e.g., the hydrogel forming polymer particles and coated hydrogel polymer particles) and then, by use of equipment described herein, one can visually distinguish the particles with a non-breaking coating and the material without non-breaking coating, and separate these into two fraction and then determine the weight of each fraction and determine the weight percentage of hydrogel forming polymer particle which are coated with a non-breaking coating, as described herein, e.g., by mere counting and calculating.

In practice, when using the method described herein, the coating of a swollen coated hydrogel-forming polymer particle is observed as, and considered as, non-breaking when either: at least 80% of the surface of a (swollen) hydrogel forming polymer particles is covered by the elastomeric, polymeric coating; and/or when the coating is observed as completely continuous and/or completely connecting and/or completely circumscribing the core of the particle; and/or when no break lines or cracks, which divide the coating into two separate parts, are observed.

Typically, the coating layer or shell of is connected; more preferably, the coating shell is connected and completely circumscribing the hydrogel forming polymer (s), both before and after swelling in 0.9% saline, by the method described herein.

For the purpose of a preferred embodiment of this invention, the coating is considered connected when for each two points P1 and P2 that are in the coating of a hydrogel forming polymer particle, there is at least one continuous line that connects these points P1 and P2 and that completely lies within the coated shell.

For the purpose of a preferred embodiment of this invention, the coating is considered completely circumscribing the hydrogel forming polymer(s) when for each point P3 positioned in the hydrogel forming polymer (and thus not on or in the coating shell or layer) and for each point P4 outside the coated hydrogel forming polymer particle or water-swellable material, all continuous bands having a circular cross-section that connect P3 and P4 and that have a diameter of 500 μm, or preferably even only 100 μm, will intersect the coated layer/shell. (A band is defined as a line with a circular cross-section.)

It should be understood for the purpose of the invention that not all hydrogel forming polymers in the water-swellable material has to be coated with the coating agent herein.

However, at least 60% of the hydrogel forming polymer particles, coated with the coating agent herein, have a non-breaking coating, when the water-swellable material (as a whole) is swollen to equilibrium in a 0.9% saline solution. Preferably this percentage is even higher, e.g., at least 70%, or even at least 80% or even at least 90% or even at least 95%.

For the purpose of the invention, the hydrogel forming polymers of which at least a part is coated is herein referred to as 'coated hydrogel forming polymers (particles)', unless specifically defined differently.

The coating agent is preferably present at a level of 1% to 50% by weight of the water-swellable material, more preferably from 1% to 30% by weight or even from 1% to 20% by weight or even from 2% to 15% by weight.

In particular in this embodiment, the coating materials and the resulting coatings are preferably highly water permeable such as to allow a fast penetration/absorption of liquid into the water swellable material (into the core).

In another preferred embodiment of the invention, the coating shell is porous and in the form of a network comprising pores for penetration of water, such as for example in the form of a fibrous network, that is connected and circumscribing the particle as defined above.

The coating agent is applied such that the resulting coating layer is preferably thin; preferably the coating layer has an average caliper (thickness) between 1 micron to 200 microns (μm), more preferably from 1 micron to 100 microns or even to 50 microns or even to 20 microns, or in certain embodiments, even more preferably from 2 to 15 microns.

The coating is preferably uniform in caliper and/or shape. Preferably, the average caliper is such that the ratio of the smallest to the largest caliper is between 1:5 to 1:1, preferably 1:2 to 1:1. Thus, preferred is that the average caliper or thickness is in about the same range as cited above.

The water-swellable material of the invention may also comprise other components, such as fillers, flowing aids, process aids, anti-caking agents, odor control agents, colouring agents, coatings to impart wet stickiness, hydrophilic surface coatings, etc. However, the hydrogel forming polymer particles of which at least a part is coated, are preferably present in the water-swellable material at a level of at least 60% by weight (of the water-swellable material), more preferably between 70% and 100% by weight or even from 80% to 100% by weight, and most preferably between 90% and 100% by weight.

The water-swellable material is typically solid; this includes gels, flakes, fibres, agglomerates, large blocks, granules and particles, spheres and other forms known in the art for superabsorbent or water-swellable polymers described herein.

Preferably, the material is in the form of particles having a mass median particle size between 10 μm and 1 mm, preferably between 100 μm and 800 μm, as can for example be measured by the method set out in for example EP-A-0691133.

In one embodiment of the invention the water swellable material of the invention is in the form of (free flowing) particles with particle sizes between 10 m and 1200 m or even between 50 μm and 800 μm and a mass median particle size between 100 and 600 μm.

In addition, or in another embodiment of the invention, the water swellable material comprises particles that are essentially spherical.

In yet another preferred embodiment of the invention the water swellable material of the invention has a relatively narrow range of particle sizes with the majority of particles having a particle size between 50 μm and 800 μm, preferably between 100 μm and 500 μm, and more preferably between 200 μm and 500 μm.

The water-swellable material of the invention preferably comprises less than 20% by weight of water, or even less than 10% or even less than 8% or even less than 5%, or even no water. The water-content of the water-swellable material can be determined by the EDANA test, number ERT 430.1-99 (February 1999) which involves drying the water swellable material at 105 Celsius for 3 hours and determining the moisture content by the weight loss of the water swellable materials after drying.

Preferred may be that the water-swellable material comprises two coatings, obtainable by coating the hydrogel forming polymers twice or more. This may be the same coating agent or a different coating agent. For example, the coating may be formed by two layers or coatings of polymeric elastomeric material, as described herein below, or it may have a first layer or shell of polymeric elastomeric material and a second layer of an organic or inorganic powder, such as various salts, silicates, clay, etc.

Especially preferred water swellable materials of the invention have a high sorption capacity measured by the CCRC test outlined below, e.g., of 50 g/g or more, or even 60 g/g or even 80 g/g or even 100 g/g.

Especially preferred water swellable materials of the invention have a high permeability for liquid such as can be measured by the SFC test disclosed in U.S. Pat. No. 5,599,335, U.S. Pat. No. 5,562,646 and U.S. Pat. No. 5,669,894 all of which are incorporated herein by reference.

In addition, especially preferred water swellable materials of the invention have a high wet porosity (i.e. this means that once an amount of the water-swellable material of the invention is allowed to absorb a liquid and swell, it will typically form a (hydro)gel or (hydro)gelbed, which has thus a certain wet porosity, in particular compared to the uncoated water-swellable polymers, as can be measured by the PHL test disclosed in U.S. Pat. No. 5,562,646 which is incorporated herein by reference (if the water-swellable material or hydrogel forming polymers are to be tested at different pressures, the weight used in this test should be adjusted accordingly).

The use of the coating agent preferably increases the wet porosity of the water-swellable material herein, compared to the uncoated hydrogel forming polymers; preferably this increase is at least 50% or even at least 100%, or even at least 150%.

Most preferred water swellable materials made by the process of the invention have a high absorption capacity such as preferably measured by the CCRC test outlined below in combination with a high permeability (SFC) and high wet porosity (increased by the use of the coating agent).

Hydrogel Forming Polymers

The hydrogel-forming polymers herein are preferably solid, preferably in the form of particles, flakes, fibres, agglomerated particles; most preferably, the polymers are particles having a mass median particle size as specified above for the water-swellable material, but slightly increased by the caliper of the coating as described herein.

As used herein, the term "hydrogel forming polymer" and "coated hydrogel forming polymer" refers to a polymer which is substantially water-insoluble, water-swellable and water-gelling, forming a hydrogel, and which has typically a Cylinder Centrifuge Retention Capacity (CCRC) as defined below of at least 8 g/g, or even at least 10 g/g/ or even at least 20 g/g. These polymers are often also referred to in the art as (super-) absorbent polymers (SAP) or absorbent gelling materials (AGM).

These polymers are typically (lightly) crosslinked polymers, preferably lightly crosslinked hydrophilic polymers. While these polymers may in general be non-ionic, cationic, zwitterionic, or anionic, the preferred polymers are cationic or anionic. Especially preferred are acid polymers, which contain a multiplicity of acid functional groups such as carboxylic acid groups, or their salts, preferably sodium salts. Examples of acid polymers suitable for use herein include those which are prepared from polymerizable, acid-containing monomers, or monomers containing functional groups which can be converted to acid groups after polymerization. Such monomers include olefinically unsaturated carboxylic acids and anhydrides, and mixtures thereof. The acid polymers can also comprise polymers that are not prepared from olefinically unsaturated monomers.

Examples of such polymers also include polysaccharide-based polymers such as carboxymethyl starch and carboxymethyl cellulose, and poly(amino acid) based polymers such as poly(aspartic acid). For a description of poly(amino acid) absorbent polymers, see, for example, U.S. Pat. No. 5,247,068, issued Sep. 21, 1993 to Donachy et al.

Some non-acid monomers can also be included, usually in minor amounts, in preparing the absorbent polymers herein. Such non-acid monomers can include, for example, monomers containing the following types of functional groups: carboxylate or sulfonate esters, hydroxyl groups, amide-groups, amino groups, nitrile groups, quaternary ammonium salt groups, and aryl groups (e.g., phenyl groups, such as those derived from styrene monomer). Other optional non-acid monomers include unsaturated hydrocarbons such as ethylene, propylene, 1-butene, butadiene, and isoprene. These non-acid monomers are well-known materials and are described in greater detail, for example, in U.S. Pat. No. 4,076,663 (Masuda et al.), issued Feb. 28, 1978, and in U.S. Pat. No. 4,062,817 (Westerman), issued Dec. 13, 1977.

Olefinically unsaturated carboxylic acid and anhydride monomers useful herein include the acrylic acids typified by acrylic acid itself, methacrylic acid, α-chloroacrylic acid, a-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citroconic acid, mesaconic acid, glutaconic acid, aconitic acid, maleic acid, fumaric acid, tricarboxyethylene, and maleic anhydride.

Preferred hydrogel forming polymers contain carboxyl groups, such as the above-described carboxylic acid/carboxylate containing groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, hydrolyzed vinyl acetate-acrylic ester copolymers, hydrolyzed acrylonitrile or acrylamide copolymers, slightly network crosslinked polymers of any of the foregoing copolymers, polyacrylic acid, and slightly network crosslinked polymers of polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Most preferred polymer materials used for making the water-sellable polymers herein are polyacrylates/acrylic acids and derivatives thereof, preferably (slightly) network crosslinked polymers partially neutralized polyacrylic acids and/or -starch derivatives thereof.

Preferred may be that partially neutralized polymeric acrylic acid is used in the process herein.

The hydrogel forming polymers useful in the present invention can be formed by any polymerization and/or crosslinking techniques. Typical processes for producing these polymers are described in U.S. Reissue Pat. 32,649 (Brandt et al.), issued Apr. 19, 1988, U.S. Pat. No. 4,666,983 (Tsubakimoto et al.), issued May 19, 1987, and U.S. Pat. No. 4,625,001 (Tsubakimoto et al.), issued Nov. 25, 1986; U.S. Pat. No. 5,140,076 (Harada); U.S. Pat. No. 6,376,618 B1, U.S. Pat. No. 6,391,451 and U.S. Pat. No. 6,239,230 (Mitchell); U.S. Pat. No. 6,150,469 (Harada). Crosslinking can be affected during polymerization by incorporation of suitable crosslinking monomers. Alternatively, the polymers can be crosslinked after polymerization by reaction with a suitable reactive crosslinking agent. Surface crosslinking of the initially formed polymers is a preferred way to control to some extends the absorbent capacity, porosity and permeability.

The hydrogel forming polymers may also be surface-crosslinked, prior to, simultaneously with or after the coating step of the process herein. Suitable general methods for carrying out surface crosslinking of absorbent polymers according to the present invention are disclosed in U.S. Pat. No. 4,541,871 (Obayashi), issued Sep. 17, 1985; published PCT application WO92/16565 (Stanley), published Oct. 1, 1992, published PCT application WO90/08789 (Tai), published Aug. 9, 1990; published PCT application WO93/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308 (Makita), issued May 6, 1986; U.S. Pat. No. 4,734,478 (Tsubakimoto), issued Mar. 29, 1988; U.S. Pat. No. 5,164,459 (Kimura et al.), issued Nov. 17, 1992; published German patent application 4,020,780 (Dahmen), published Aug. 29, 1991; U.S. Pat. No. 5,140,076 (Harada); U.S. Pat. No. 6,376,618 B1, U.S. Pat. No. 6,391,451 and U.S. Pat. No. 6,239,230 (Mitchell); U.S. Pat. No. 6,150,469 (Harada); and published European patent application 509, 708 (Gartner), published Oct. 21, 1992.

Most preferably, the polymers comprise from about 50% to 95% (mol percentage), preferably about 75% neutralized, (slightly) network crosslinked, polyacrylic acid (i.e., poly (sodium acrylate/acrylic acid)). Network crosslinking renders the polymer substantially water-insoluble and, in part, determines the absorptive capacity and extractable polymer content characteristics of the absorbent polymers. Processes for network crosslinking these polymers and typical network crosslinking agents are described in greater detail in U.S. Pat. No. 4,076,663.

While the hydrogel forming polymer is preferably of one type (i.e., homogeneous), mixtures of hydrogel forming polymers can also be used in the present invention. For example, mixtures of starch-acrylic acid graft copolymers and slightly network crosslinked polymers of polyacrylic acid can be used in the present invention. Mixtures of (coated) polymers with different physical properties, and optionally also different chemical properties, could also be used, e.g., different mean particle size, absorbent capacity, absorbent speed, SFC value) such as for example disclosed in U.S. Pat. No. 5,714,156 which is incorporated herein by reference.

The hydrogel forming polymers preferably have a low amount of extractables, preferably less than 15% (by weight of the polymers; 1 hour test value), more preferably less than 10% and most preferably less than 5% of extractables, or even less than 3%. The extractables and levels thereof and determination thereof are further described in for example U.S. Pat. No. 5,599,335; U.S. Pat. No. 5,562,646 or U.S. Pat. No. 5,669,894.

Coating Agents and Polymeric Elastomeric Material

The coating agent herein comprises an elastomeric polymeric material. It is believed that the elastomeric polymeric materials provide a return force when being extended and thus enable the coating (shell/layer) to provide tangential forces around the hydrogel forming polymer, thereby thus acting like the elastic membrane of a balloon and providing a resistance to deformation for the water swellable material of the invention.

Preferred polymeric elastomeric materials herein have a glass transition temperature Tg of below 38° C., preferably less than 20° C., more preferably less than 0° C., and most preferably between 0° C. and −60° C. (i.e., Tg's before curing).

The coating agent is preferably such that the resulting coating on the hydrogel forming polymers herein is water-permeable, but not water-soluble and, preferably not water-dispersible. The water permeability of the coating should be high enough such that the coated water swellable material has a sufficiently high free swell rate as defined above, preferably a free swell rate (FSR) of at least 0.05 g/g/sec, preferably at least 0.1 g/g/sec, and more preferably at least 0.2 g/g/sec.

Preferred elastomeric, polymeric materials herein include natural or synthetic elastomeric polymeric materials, preferably elastomeric polymeric material selected from the group of natural rubber, synthetic rubber and thermoplastic elastomeric polymers that are elastic at 35° C., or below any of the temperatures above.

Preferred coating agents of the present invention comprise polymers that form a film by any film forming method known in the art, e.g., when being applied (as a spray) from a solution, dispersion or as hotmelt, for example under the process conditions described below. Further preferred are polymers that form elastomeric films that are not tacky or sticky in the dry state. Especially preferred are coating agents that are not tacky or sticky in the dry state but are sticky or tacky in the wet state.

The elastomeric polymers useful in coating agents of the present invention are preferably polymers that can be self-crosslinking, i.e., form covalent crosslinks in the polymer network to make it thermoset. Alternatively, crosslinking agents may be added to the polymers to cause crosslinking after activation, e.g., with high temperature, described hereinafter under the discussion of the curing step c).

In a preferred embodiment, the elastomeric polymers useful in coating agents of the present invention may be reactive with the water-swellable polymers, preferably thereto being a carboxylated elastomeric polymeric (elastomeric) material.

Especially preferred coating agents comprise polymers, co-polymers, and/or blockcopolymers of ethylene, vinyl compounds (e.g., styrene, vinylacetate, vinylformamide), polyunsaturated monomers (e.g., butadiene, isoprene), as well as polyurethanes, polyethers, polydimethylsiloxanes, proteins, which may optionally be grafted and/or be partially modified with chemical substituents (e.g., hydroxyl groups or carboxylates).

Highly preferred materials useful in the coating agent herein are commercially available elastomeric latex materials, such for example from the Hystretch, Vinamul, Dur-O-Set Elite, GenFlo and AcryGen series, in particular Hystretch V43, Hystretch V60, Hystretch V23, Vinamul 3301, Vinamule Dur-O-Set Elite Ultra, Vinamul Dur-O-Set Elite 21, Rovene 4151, Rovene 5550, GenFlo 3075, GenFlo 3088, GenFlo 3000, Suncryl CP-75, AcryGen DV242DX, AcryGen 1900 D.

Hystretch is a trademark of Noveon Inc., 9911 Brecksville Road, Cleveland, Ohio 44141-3247, USA. Vinamul and Dur-O-Set Elite are trademarks of Vinamul Polymers, De Asselen Kuil 20, 6161 RD Geleen, NL. Rovene is a trademark of Mallard Creek Polymers, 14700 Mallard Creek Road, Charlotte, N.C. 28262, USA. GenFlo, AcryGen and Suncryl are trademarks of Omnova Solutions Inc., 2990 Gilchrist Road, Akron, Ohio 44305-4418, USA.

Particularly preferred coating agents comprise Surface Hydrophilic Elastic Latexes (SHEL) as described for example in U.S. Pat. No. 4,734,445; U.S. Pat. No. 4,835,211, U.S. Pat. No. 4,785,030; EP 0 799 258 B1 all of which are incorporated herein by reference. These particularly preferred SHEL materials typically comprise: (1) a liquid phase selected from the group consisting of water, water-miscible solvents and mixtures thereof; and (2) an effective amount of latex particles dispersed in the liquid phase. These particles comprise an elastomeric hydrophobic core and an outer hydrophilic shell integral with the elastomeric core. The hydrophilic shell of the particles ultimately translates into the hydrophilic surface of films formed therefrom, and also advantageously stabilizes the particles as colloids in the liquid phase. The shell comprises hydrophilic moieties —X which are attached to the core via linking group L-. When the liquid phase is removed, the particles form an elastomeric film having a substantially permanent hydrophilic surface. The SHEL compositions have the desirable property of forming elastomeric films having a hydrophilic surface and surface hydrophilicity, combined with other properties such as flexibility, elasticity and strength.

Other examples of polymeric elastomeric materials include materials with elastic properties like VFE-CD, available from Tredegar, and L-86, available from Fulflex (Limerick, Ireland), or preferably L-89, available from Fulflex, or more preferred are of course one or more of these materials itself.

Also mixtures of elastomeric polymeric materials may be present in the coating agent.

The coating agent may also comprise other components, including the following.

Preferred polymeric elastomeric materials for use in the coating agent herein are strain hardening and/or strain crystallizing. While there are some elastomeric polymers that are strain crystallizing, this property can also be imparted by the addition or blending of materials into the polymer. Hereto, the coating agent may comprise additional components that increase the strain hardening and/or strain crystallization of the elastomeric polymeric material, such as organic or inorganic fillers. Nonlimiting examples of inorganic fillers include various water-insoluble salts, and other (preferably nanoparticulate) materials such as for example chemically modified silica, also called active or semi-active silica that are for example available as fillers for synthetic rubbers. Examples for such fillers are UltraSil VN3, UltraSil VN3P, UltraSil VN2P, and UltraSil 7000GR available from Degussa AG, Weißfrauenstraße 9, D-60287 Frankfurt am Main, Germany.

The coating agent is preferably hydrophilic and in particular surface hydrophilic. The surface hydrophilicity may be determined by methods known to those skilled in the art. In a preferred execution, the hydrophilic coating agents or elastomeric polymeric materials are materials that are wetted by the liquid that is to be absorbed (0.9% saline; urine). They may be characterized by a contact angle that is less than 90 degrees. Contact angles can for example be measured with the Video-based contact angle measurement device, Krüss G10-G1041, available from Kruess, Germany or by other methods known in the art.

It may also be preferred that the resulting water-swellable material or coated hydrogel forming polymer particles are hydrophilic. This hydrophilicity may be measured as described in co-pending U.S. patent application Ser. No. 10/881,090.

If the coating agent itself is not hydrophilic, it can be made hydrophilic for example by treating it with surfactants, plasma coating, plasma polymerization, or other hydrophilic surface treatments as known to those skilled in the art.

Preferred compounds to be added to make the hydrophilic coating agent, or subsequently to be added to the resulting coated hydrogel forming polymers are for example: N-(2-Acetamido)-2-aminoethansulfonic-acid, N-(2-Acetamido)-imino-di-acetic-acid, N-acetyl-glycin, B-Alanin, Aluminum-hydroxy-acetat, N-Amidino-glycin, 2-Amino-ethyl-hydrogenphosphate, 2-Amino-ethyl-hydrogensulfate, Amino-methan-sulfonic-acid, Maleinic-acid, Arginin, Asparaginic-acid, Butane-di-acid, Bis(1-aminoguanidinium)-sulfat, 2-Oxo-propionic-acid, Tri-Calcium-di-citrat, Calciumgluconat, Calcium-saccharat, Calcium-Titriplex®, Camitin, Cellobiose, Citrullin, Creatin, Dimethylaminoacetic acid, THAM-1,2-disulfonic-acid, Ethylendiammonium-sulfate, Fructose, Fumaric-acid, Galactose, Glucosamine, Gluconic-acid, Glutamine, 2-Amino-glutaric-acid, Glutaric-acid, Glycin, Glycylglycin, Imino-di-acetic-acid, Magnesium-glycerophosphate, Oxalicacid, Tetrahydroxy-adipinic-acid, Taurin, N-Methyl-taurin, Tris-(hydroxymethyl)-aminomethan, N-(Tris-(hydroxymethyl)-methyl)-2-aminoethansulfonicacid.

Alternatively, the coating agent can be made hydrophilic with a hydrophilicity boosting composition comprising a hydrophilicity-boosting amount of nanoparticles. By hydrophilicity boosting amount, it is intended that an amount of nanoparticles be present in the hydrophilicity boosting compositions, which are sufficient to make a substrate to which it is applied more hydrophilic. Such amounts are readily ascertained by one of ordinary skill in the art; it is based on many factors, including but not limited to, the substrate used, the nanoparticles used, the desired hydrophilicity of the resulting coated water-swellable material.

Nanoparticles are particles that have a primary particle size (diameter), which is in the order of magnitude of nanometers. That is, nanoparticles have a particle size ranging from about 1 to about 750 nanometers. Nanoparticles with particle sizes ranging from about 2 nm to about 750 nm can be economically produced. Non-limiting examples of particle size distributions of the nanoparticles are those that fall within the range from about 2 nm to less than about 750 nm, alternatively from about 2 nm to less than about 200 nm, and alternatively from about 2 nm to less than about 150 nm.

The particle size of the nanoparticles is the largest diameter of the nanoparticle and may be measured by any method known to the skilled person.

The mean particle size of various types of nanoparticles may differ from the individual particle size of the nanoparticle. For example, a layered synthetic silicate can have a mean particle size of about 25 nanometers while its particle size distribution can generally vary between about 10 nm to about 40 nm. (It should be understood that the particle sizes that are described herein are for particles when they are dispersed in an aqueous medium and the mean particle size is based on the mean of the particle number distribution. Non-limiting examples of nanoparticles can include crystalline or amorphous particles with a particle size from about 2 to about 750 nanometers. Boehmite alumina can have an average particle size distribution from 2 to 750 nm.).

If the hydrophilicity boosting composition does not consist of the nanoparticles, but comprises other ingredients, then it is preferred that the nanoparticles are present in the hydrophilicity boosting compositions, or when added to the coating agent, at levels of from about 0.0001% to about 50%, preferably from about 0.001% to about 20% or even to 15%, and more preferably from about 0.001% to about 10%, by weight of the composition or the coating agent.

Either organic or inorganic nanoparticles may be used in the hydrophilicity boosting composition; inorganic nanoparticles are preferred. Inorganic nanoparticles generally exist as oxides, silicates, carbonates and hydroxides. Some layered clay minerals and inorganic metal oxides can be examples of nanoparticles. The layered clay minerals suitable for use in the present invention include those in the geological classes of the smectites, the kaolins, the illites, the chlorites, the attapulgites and the mixed layer clays. Typical examples of specific clays belonging to these classes are the smectices, kaolins, illites, chlorites, attapulgites and mixed layer clays. Smectites, for example, include montmorillonite, bentonite, pyrophyllite, hectorite, saponite, sauconite, nontronite, talc, beidellite, volchonskoite. Kaolins include kaolinite, dickite, nacrite, antigorite, anauxite, halloysite, indellite and chrysotile. Illites include bravaisite, muscovite, paragonite, phlogopite and biotite and vermiculite. Chlorites include corrensite, penninite, donbassite, sudoite, pennine and clinochlore. Attapulgites include sepiolite and polygorskyte. Mixed layer clays include allevardite and vermiculitebiotite. Variants and isomorphic substitutions of these layered clay minerals offer unique applications.

Layered clay minerals may be either naturally occurring or synthetic. An example of one non-limiting embodiment of the coating composition uses natural or synthetic hectorites, montmorillonites and bentonites. Another embodiment uses the hectorites clays commercially available, and typical sources of commercial hectorites are the LAPONUEs™ from Southern Clay Products, Inc., U.S.A; Veegum Pro and Veegum F from R. T. Vanderbilt, U.S.A.; and the Barasyms, Macaloids and Propaloids from Baroid Division, National Read Comp., U.S.A.

In one preferred embodiment of the present invention the nanoparticles comprise a synthetic hectorite a lithium magnesium silicate. One such suitable lithium magnesium silicate is LAPONITE™, which has the formula:

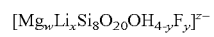
$$[Mg_wLi_xSi_8O_{20}OH_{4-y}F_y]^{z-}$$

wherein w=3 to 6, x=0 to 3, y=0 to 4, z=12-2w-x, and the overall negative la is balanced by counter-ions; and wherein the counter-ions are selected from the group consisting of selected $Na^+$, $K^+$, $NH_4+$, $Cs^+$, $Li^+$, $Mg^{++}$, $Ca^{++}$, $Ba^{++}$, $N(CH_3)_4^+$ and mixtures thereof. (If the LAPONITE™ is "modified" with a cationic organic compound, then the "counter-ion" could be viewed as being any cationic organic group ($R^+$).)

Other suitable synthetic hectorites include, but are not limited to isomorphous substitutions of LAPONITE™, such as, LAPONITE B™, LAPONITE S™, LAPONITE XLS™, LAPONITE RD™, LAPONITE XLG™, and LAPONITE RDS™.

The nanoparticles may also be other inorganic materials, including inorganic oxides such as, but not limited to, titanium oxide silica, zirconium oxide, aluminum oxide, magnesium oxide and combinations thereof. Other suitable inorganic oxides include various other inorganic oxides of alumina and silica.

In one preferred embodiment of the present invention the nanoparticles comprise a Boehmite alumina ($[Al(O)(OH)]_n$) which is a water dispersible, inorganic metal oxide that can be prepared to have a variety of particle sizes or range of particle sizes, including a mean particle size distribution from about 2 nm to less than or equal to about 750 nm. For example, a boehmite alumina nanoparticle with a mean particle size distribution of around 25 nm under the trade name Disperal P2™ and a nanoparticle with a mean particle size distribution of around 140 nm under the trade name of Dispal™ 14N4-25 are available from North American Sasol, Inc.

In one preferred embodiment of the present invention the nanoparticles are selected from the group consisting of titanium dioxide, Boehmite alumina, sodium magnesium lithium fluorosilicates and combinations thereof.

Use of mixtures of nanoparticles in the hydrophilicity boosting compositions is also within the scope of the present invention.

The hydrophilicity boosting compositions of the present invention may also include optional ingredients such as, a carrier, surfactant and other adjunct ingredients. Suitable carriers include liquids, solids and gases. One preferred carrier is water, which can be distilled, deionized, or tap water. Water is valuable due to its low cost, availability, safety, and compatibility.

Optionally, in addition to or in place of water, the carrier can comprise a low molecular weight organic solvent. Preferably, the solvent is highly soluble in water, e.g., ethanol, methanol, acetone, ethylene glycol, propanol, isopropanol, and the like, and mixtures thereof. Low molecular weight alcohols can reduce the surface tension of the nanoparticle dispersion to improve wettability of the substrate. This is particularly helpful when the substrate is hydrophobic. Low molecular weight alcohols can also help the treated substrate to dry faster. The optional water soluble low molecular weight solvent can be used at any suitable level. The carrier can comprise any suitable amount of the composition, including but not limited to from about 10% to about 99%, alternatively from about 30% to about 95%, by weight of the coating composition.

The hydrophilicity boosting composition may also comprise organic, e.g., latex nanoparticles, so-called nanolatexes. A "nanolatex", as used herein, is a latex with a particle size less than or equal to about 750 nm. A "latex" is a dispersion of water-insoluble polymer particles that are usually spherical in shape. Nanolatexes may be formed by emulsion polymerization.

"Emulsion polymerization" is a process in which monomers of the latex are dispersed in water using a surfactant to form a stable emulsion followed by polymerization. Particles are typically produced which can range in size from about 2 to about 600 nm. When the nanolatexes are elastomeric polymers, then they are considered coating agents for the purpose of the invention, and not (part of) a hydrophilicity boosting compositions.

Surfactants are especially useful in the coating composition as wetting agents to facilitate the dispersion of nanoparticles onto the substrate. Surfactants are preferably included when the coating composition is used to treat a hydrophobic substrate.

Suitable surfactants can be selected from the group including anionic surfactants, cationic surfactants, nonionic surfactants, amphoteric surfactants, ampholytic surfactants, zwitterionic surfactants and mixtures thereof. Nonlimiting examples of surfactants useful in the compositions of the present invention are disclosed in McCutcheon's, Detergents and Emulsifiers, North American edition (1986), published by Allured Publishing Corporation; McCutcheon's, Functional Materials, North American Edition (1992); U.S. Pat. Nos. 5,707,950 and 5,576,282; and U.S. Pat. No. 3,929,678, to Laughlin et al., issued Dec. 30, 1975.

When a surfactant is used in the coating agent, it may be added at an effective amount to provide facilitate application of the coating composition. Surfactant, when present, is typically employed in compositions at levels of from about 0.0001% to about 60%, preferably from about 0.001% to about 35%, and more preferably from about 0.001% to about 25%, by weight of the coating agent.

Nonlimiting examples of surfactants include nonionic and amphoteric surfactants such as the $C_{12}$-$C_{18}$ alkyl ethoxylates ("AE") including the so-called narrow peaked alkyl ethoxylates and $C_6$-$C_{12}$ alkyl phenol alkoxylates (especially ethoxylates and mixed ethoxy/propoxy), $C_{12}$-$C_{18}$ betaines and sulfobetaines ("sultaines"), $C_{10}$-$C_{18}$ amine oxides, and the like. Another class of useful surfactants is silicone surfactants and/or silicones. They can be used alone and/or alternatively in combination with the alkyl ethoxylate surfactants described herein. Nonlimiting examples of silicone surfactants are the polyalkylene oxide polysiloxanes having a dimethyl polysiloxane hydrophobic moiety and one or more hydrophilic polyalkylene side chains, and having the general formula:

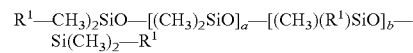

wherein a+b are from about 1 to about 50, and each $R^1$ is the same or different and is selected from the group consisting of methyl and a poly(ethyleneoxide/propyleneoxide) copolymer group having the general formula: —$(CH_2)_nO(C_2H_4O)_c(C_3H_6O)_dR^2$, wherein n is 3 or 4; total c (for all polyalkyleneoxy side groups) has a value of from 1 to about 100, alternatively from about 6 to about 100; total d is from 0 to about 14; alternatively d is 0; total c+d has a value of from about 5 to about 150, alternatively from about 9 to about 100 and each $R^2$ is the same or different and is selected from the group consisting of hydrogen, an alkyl having 1 to 4 carbon atoms, and an acetyl group, alternatively hydrogen and methyl group. Each polyalkylene oxide polysiloxane has at least one $R^1$ group being a poly(ethyleneoxide/propyleneoxide) copolymer group. Silicone superwetting agents are available from Dow Corning as silicone glycol copolymers (e.g., Q2-5211 and Q2-5212).

The coating agent is preferably applied in fluid form, e.g., as melt (or so-called hotmelt), solution or dispersion. Preferred are water-based solutions or dispersions. In the context of this invention and as it is typically used in the art, the latexes referred herein are thus typically applied as water based dispersions of specific latex polymers, whereby the polymeric latex particles—typically of spherical shape—are suspended or dispersed (stable) in a water based liquid.

Thus, the coating agent may also comprise a solvent or dispersing liquid, such as water, THF (tetrahydrofurane), cyclohexane or other solvents or dispersing liquids that are able to dissolve or disperse the elastomeric polymer and subsequently can be evaporated such as to form a (dry) coating shell or layer.

As it is known to those skilled in the art, in particular for latex dispersions with lower amounts of the polymer in the water dispersion, the viscosity is decreased, which enables good spreading of the coating agent. On the other hand, it is preferred to have higher amounts of polymer in the water dispersion to aid film quality and coalescence, and to minimize the amount of liquid that needs to be dried-off or evaporated. Thus, the skilled person would know how to select a high enough but not to low concentration to obtain the desired coating.

Preferably, the coating agent comprises from 0% to 95% by weight of a dispersing liquid or solvent, such as water. Preferred is that the coating agent comprises at least 10% by weight (of the coating agent) of the polymeric elastomeric material, more preferably from 20% to 80% or even from 30% to 70%, the remaining percentage being said liquid and/or fillers/hydrophilicity aids, spreading aids, etc., as described herein.

Process of the Invention for Making the Solid Water-Swellable Material

The water-swellable material of the inventions may be made by any known process.

A preferred coating process for coating the hydrogel forming polymers herein involves:

a) obtaining hydrogel forming polymers; and b) simultaneously with or subsequently to step a), applying a coating agent comprising an elastomeric polymeric material to at least part of said hydrogel forming polymers to obtain coated hydrogel forming polymers; and preferably c) prior to, simultaneous with or subsequent to step b), obtaining said hydrogel forming polymers or coated hydrogel forming polymers in solid, preferably particulate, form.

In step a) 'obtaining' the hydrogel forming polymers, as described herein above, includes using commercially available hydrogel forming polymers, or forming the hydrogel forming polymers by any known process from precursors. It includes also for example the possibility that step a) and b) are done simultaneously and that step a) involves reacting the relevant polymer precursors to form the hydrogel forming polymer in the same reaction conditions/medium as the coating step b) (for example, the polymer precursors and coating agent can be mixed together).

It should be noted that optional process steps may take place prior to, or simultaneous with step a) and/or b) and/or c), such as that the hydrogel forming polymer may be surface crosslinked prior to step b) or that the coating agent or hydrogel forming polymers may be submitted to a hydrophilic treatment, to render them more hydrophilic, prior to step b).

The coating step b) may be done by any known method, for example by mixing or dispersing the hydrogel forming polymers (or precursors thereto) in the coating agent or melt or solution or dispersion thereof; by spraying the coating agent or (hot) melt, solution or dispersion thereof onto the polymers; by introducing the coating agent, or melt, dispersion or solution thereof, and the hydrogel forming polymers (or precursors thereto) in a fluidised bed or Wurster coater; by agglomerating the coating agent, or melt, solution or dispersion thereof, and the hydrogel forming polymers (or precursors thereof); by dip-coating the (particulate) hydrogel forming polymers in the coating agent, melt, dispersion or solution thereof. Other suitable mixers include for example twin drum mixers, so called "Zig-Zag" mixers, horizontally operating plough-share mixers, Lödige mixers, cone screw mixers, or perpendicularly cylindrical mixers having coaxially rotating blades. Examples of preferred coating processes are for example described in U.S. Pat. No. 5,840,329 and U.S. Pat. No. 6,387,495.

In an alternative embodiment of the invention, the coating step b) may be done by applying the coating agent in the form of a foam, preferably in the form of an open-cell foam, leading to a porous coating. In yet an alternative embodiment the coating step may be done by forming a fibrous network on the surface of the hydrogel forming polymers such as for example by applying the coating agent in the form of meltblown microfibers, such that an essentially connected coating is formed (as described herein).

In a yet another embodiment, the coating step b) may be done by applying a coating agent that comprises polymerizable material, polymerizable into elastomeric polymeric material (such as the monomers of such polymeric material, as described herein) and directly polymerising these on the surface of the hydrogel forming polymers.

The coating agents may also comprise solvents such as organic or optionally water-miscible solvents. Suitable organic solvents are, for example, aliphatic and aromatic hydrocarbons, alcohols, ethers, esters, and ketones. Suitable water-miscible solvents are, for example, aliphatic alcohols, polyhydric alcohols, ethers, and ketones.

If the coating agent is in the form of a latex dispersion, it may be further preferred to add processing aids (such for example coalescing aids) subsequently or prior to the coating step b) in order to aid a good film formation of the coating layer.

The process may comprise a curing step (d) which typically results in a further strengthened or more continuous or more completely connected coating. For example, during the curing step the coating may be annealed or cross-linked, as described below in more detail.

The curing step may be done by any known method. Typically, the curing step involves a heat treatment of the resulting coated hydrogel forming polymers; it may be done by for example radiation heating, oven heating, convection heating, or placing the coated polymers under vacuum and increased temperature, azeotropic heating, and it may for example take place in conventional equipment used for drying, such as fluidized bed driers.

Preferred may be that a vacuum is applied as well or that the curing or drying is done under an inert gas (to avoid oxidation).

Preferably, the heat treatment involves heating the coated hydrogel forming polymers at a temperature of at least 70° C., or even at least 80° C., or even at least 100° C., or even at least 120° C. or even at least 130° C. or even at least 140° C., and preferably for at least 5 minutes, or even for at least 10 minutes or even for at least 15 minutes, or even at least 30 minutes or even at least 1 hour or even at least 2 hours. Preferred is that the maximum temperature is up to 300° C., or even up to 250° C. or even up to 200° C.

This heat-treatment may be done once, or it may be repeated, for example the heat treatment may be repeated with different temperatures, for example first at a lower temperature, for example from 70° C. or 80° C. to 100° C., as described above, for example for at least 1 hour, and subsequently at a higher temperature, for example 120-140° C. or even up to 300° C., for at least 10 minutes, to invoke chemical reactions, such as further polymerising or cross-linking the wet-extensible polymers of the coating agent.

In one preferred embodiment, the drying step may be done first at a temperature of 80-100° C. for any time, preferably at least 1 hour and preferably up to 48 hours, and the curing step (involving for example annealing/cross-linking) may be done at a temperature from 120-300° C. or even from 130-250° C., or even from 140-200° C., for at least 5 minutes, or even at least 15 minutes or even at least 30 minutes, or preferably at least 1 hour, preferably up to 4 hours or even up to 12 hours.

During the curing step, the coated hydrogel forming polymers may also be dried at the same time, but in a preferred embodiment, the coated hydrogel forming polymers are submitted to a separate drying step, prior to the coating step, which involves any of the treatments described above as curing treatment, or preferably a vacuum treatment or heat treatment at a temperature below the curing temperatures above, and typically for a time period which is longer than the curing time.

Preferably, when the coating agent is a film-forming agent or comprises a film forming elastomeric material, the curing and/or drying temperature is typically above the minimum film forming temperature (MFFT) of the coating agent or material thereof.

The resulting water-swellable material is preferably solid and thus, if the hydrogel forming polymers of step a) or the resulting coated polymers of step b) are not solid, a subsequent process step is required to solidify the resulting coated polymers of step b), e.g., a so-called solidifying or preferably particle forming step, as known in the art. This may preferably be done prior to, or simultaneously with step c).

The solidifying step includes for example drying the hydrogel forming polymers and/or the coated polymers of step b) (e.g., if the step b) involve a dispersion, suspension or solution of any of the ingredients) by increasing the temperature and/or applying a vacuum, as described herein. This may be simultaneously with, or occur automatically with the curing step c). The solidifying step may also include a cooling step, if for example a melt is used.

Subsequently, any known particle forming process may also be used here for, including agglomeration, extrusion, grinding and optionally followed by sieving to obtain the required particle size distribution.

The inventors found another preferred way to provide coatings with elastomeric material on cores of hydrogel forming polymers, namely by providing a coating that has a significantly larger surface area than the outer surface area of the hydrogel forming polymer (core), so that when the polymers swell, the coating can 'unfold' and extend. The inventors found a very easy and convenient way to provide such coated hydrogel forming polymers, namely by applying the coating agent on hydrogel forming polymers, which are in swollen state due to absorption of a liquid (e.g., water), and then removing the water or part thereof, so that the hydrogel forming polymers (in the core) shrink again, but the coating maintains its original surface area. The surface are of the coating is then larger than the surface area of the polymer core, and the coating is then typically wrinkled; it can unwrinkle when the hydrogel forming polymers absorb water and swell, without encountering any strain/stress on the coating due to the swelling of the hydrogel forming polymers.

A highly preferred process thus involves the step of obtaining hydrogel forming polymers and immersing these in a dispersion or solution of a coating agent containing a liquid (water), such as the latex dispersions described above, typically under thorough stirring. The hydrogel forming polymers will absorb the liquid, and thereby, the elastomeric material of the coating agent (latex polymer) is automatically 'transferred' to the surface of hydrogel forming polymers (particles). The amount of hydrogel forming polymers and amount of water and latex can be adjusted such that the hydrogel forming polymers can absorb about all water present in the dispersion and that when this is achieved, the hydrogel forming polymers, coated with the latex, are in the form of a gel "powder". The resulting coating is typically under zero strain/stress.

The process may also involve addition of further processing aids in any of the steps, such as granulation aids, flow aids, drying aids. For some type of coating agents, the coated hydrogel forming polymers may potentially form agglomerates. Any flow aids known in the art may be added (for example prior to or during the coating step, or preferably during the drying and/or annealing and/or cross-linking step (s), as discussed below), for example Aerosil 200, available from Degussa has been found to be a good flow aid.

Also, it may be useful to mechanically agitate the coated polymers during the curing or drying step, such as by stirring.

Highly preferred may be that the process involves addition of a spreading aid and/or surfactant, which facilitates the coating step b).

Preferred (Disposable) Absorbent Articles and Structures

The absorbent structure of one embodiment of the invention is typically for use in disposable absorbent articles, such as preferably interlabial products, sanitary napkins, panty liners, and preferably adult incontinent products, baby diapers, nappies and training pants.

Typically, the absorbent structure of the invention is that part of an absorbent article which serves to store the bodily fluid, e.g., the storage layer of an absorbent article. As known in the art, this may be in direct contact with an acquisition layer, or in one embodiment of the invention, it may form a unitary structure with an acquisition layer. In yet another embodiment of the invention the absorbent structure is an acquisition layer for use in an absorbent article.

The absorbent structure may comprise the water-swellable material of the invention at any weight level or concentration, but preferably, in particular when the absorbent structure serves as a storage layer, or when the absorbent structure comprises a layer that serves as storage layer, the structure or layer comprises large amounts of the water-swellable material herein, compared to possible other components of the structure, i.e. preferably more than 50% or even more than 70% or even more than 80% or even more than 90% of the water-swellable material herein, by weight of the structure or (storage) layer thereof.

For example, the water-swellable material may be mixed with absorbent fibrous material, such as an airfelt material, which can provide a matrix for immobilization of the water-swellable material. However, preferably a relatively low amount of absorbent fibrous (cellulose) material is used in the absorbent structure. Thus, if the absorbent structure is a liquid storage layer or when the absorbent structure comprises one or more liquid storage layers, it may be preferred that said liquid structure or said liquid storage layer comprises large amounts of the super absorbent material herein and only very little or no absorbent (cellulose) fibres, e.g., preferably less than 40% weight of that layer, or even less than 20% by weight or even less than 10 weight % or even less than 5% by weight of absorbent fibrous (cellulose) material, and preferably more than 50% or even more than 70% or even more than 80% or even more than 90% by weight of the water-swellable material herein.

The absorbent structure may comprise a wrapping material, which wraps the portion comprising the water-swellable material, a so-called core wrap material. In one preferred embodiment the core wrap material comprises a top layer and a bottom layer, being furthest away from the skin of the user. The core wrap material, the top layer or the bottom layer can be provided from a non-woven material. One preferred material is a so-called SMS material, comprising a spunbonded, a melt-blown and a further spunbonded layer. Highly preferred are permanently hydrophilic non-wovens, and in particular nonwovens with durably hydrophilic coatings. An alternative preferred material comprises a SMMS-structure. The top layer and the bottom layer may be provided from two or more separate sheets of materials or they may be alternatively provided from a unitary sheet of material.

Preferred non-woven materials are provided from synthetic fibers, such as PE, PET and most preferably PP. As the polymers used for nonwoven production are inherently hydrophobic, they are preferably coated with hydrophilic coatings, e.g., coated with nanoparticles, as known in the art.

Notably, permanently hydrophilic non-wovens are also useful in other parts of an absorbent article, for example, as or in the topsheet.

In a preferred embodiment of the present invention the absorbent structure comprises a wrapping material, the water-swellable material, described herein, and a thermoplastic material and/or a layer of adhesive, which may be a (non-absorbing) fibrous layer of adhesive.

Preferred absorbent structures can for example be made as follows:
 a) providing a substrate material that can serve as a wrapping material;
 b) depositing water-swellable material onto a first surface of the substrate material, preferably in a pattern comprising at least one zone which is substantially free of water-swellable material, and the pattern comprising at least one zone comprising water-swellable material, preferably such that opening are formed between the separate zones with water-swellable material;
 c) depositing a thermoplastic material onto the first surface of the substrate material and the water-swellable material, such that portions of the thermoplastic material are in direct contact with the first surface of the substrate and portions of the thermoplastic material are in direct contact with the water-swellable material;
 d) and then typically closing the above by folding the substrate material over, or by placing another substrate matter over the above.

Preferred disposable absorbent article herein are sanitary napkins, panty liners, adult incontinence products and infant diapers or training or pull-on pants, whereby articles which serve to absorb urine, e.g., adult incontinence products, diapers and training or pull-on pants are most preferred articles herein.

Preferred articles herein have a topsheet and a backsheet, which each have a front region, back region and crotch region, positioned therein between. The absorbent structure of the invention is typically positioned in between the topsheet and backsheet. Preferred backsheets are vapour pervious but liquid impervious. Preferred topsheet materials are at least partially hydrophilic; preferred are also so-called apertured topsheets. Preferred maybe that the topsheet comprises a skin care composition, e.g., a lotion.

These preferred absorbent articles typically comprise a liquid impervious (but preferably gas or water vapour pervious) backsheet, a fluid pervious topsheet joined to, or otherwise associated with the backsheet, and the absorbent structure according to the present invention positioned between the backsheet and the topsheet. Such articles are well known in the art and fully disclosed in various documents mentioned throughout the description, e.g., in EP 752 892.

A preferred diaper or training pants herein has a front waist band and a back waist band, whereby the front waist band and back waist band each have a first end portion and a second end portions and a middle portion located between the end portions, and whereby preferably the end portions comprise each a fastening system, to fasten the front waist band to the rear waist band or whereby preferably the end portions are connected to one another, and whereby the middle portion of the back waist band and/or the back region of the backsheet and/or the crotch region of the backsheet comprises a landing member, preferably the landing member comprising second engaging elements selected from loops, hooks, slots, slits, buttons, magnets. Most preferred are hooks, adhesive or cohesive second engaging elements. Preferred may be that the engaging elements on the article, or preferably diaper are provided with a means to ensure they are only engage able at certain moments, for example, they may be covered by a removable tab, which is removed when the engaging elements are to be engaged and may be re-closed when engagement is no longer needed, as described above.

Preferred diapers and training pants herein have one or more sets of leg elastics and/or barrier leg cuffs, as known in the art.

Preferred may also be that the topsheet has a large opening, preferably with elastication means along the length thereof, where through waist material can pass into a void space above the absorbent structure, and which ensures it is isolated in this void space, away from the wearer's skin.

Process Examples and Materials Made by the Process

Preparation of Hydrogel Forming Polymers that are Especially Useful for Use in Process Step a) of the Invention.

EXAMPLE 1.1

Process for Preparation of Spherical Hydrogel Forming Polymer Particles

Spherical core polymer particles may be obtained by UMSICHT (Fraunhofer Institut Umwelt-, Sicherheits-, Energietechnik, Oberhausen, Germany), or made by following the adapted procedure below:

40 g glacial acrylic acid (AA) is placed into a beaker, and 1712 mg MethyleneBisAcrylAmide (MBAA) is dissolved in the acid. Separately, 13.224 g solid NaOH is dissolved in 58.228 g water and cooled. The NaOH solution is then slowly added to the acrylic acid, and the resulting solution chilled to 4-10° C.

In a second beaker, 400 mg ammoniumperoxodisulfate (APS) and 400 mg sodiummetabisulfite are mixed and dissolved in 99.2 ml water. This solution is also chilled to 4-10° C.

With the use of two equal peristaltic pumps, both solutions are combined and pumped at equal rates through a short static mixer unit, after which they are dropped as individual droplets into 60-80° C. hot silicone oil (Roth M 50, cat. # 4212.2) which is in a heated, about 2 m long, glass tube. The pump rate is adjusted such that individual droplets sink through the oil in the tube, while also avoiding premature polymerization in the mixer unit. The polymerization proceeds during the descent of the droplets through the oil, and particles (gelled polymer droplets) are formed, which can be collected in a heated 1 liter Erlenmeyer flask attached to the bottom of the tube.

After completion of the addition, the oil is allowed to cool, and the spheres are collected by draining the oil. Excess oil is removed by washing with i-propanol, and the particles (spheres) are pre-dried by exposing them to excess i-propanol for 12-24 hours. Additional washings with i-propanol may be needed to remove traces of the silicone oil. The particles (spheres) are then dried in a vacuum oven at 60-100° C. until a constant weight is obtained.

The amount of MBAA may be adjusted, depending on what properties are required from the resulting polymers, e.g., when 0.3 mol % (per mol AA) MBAA is used, the resulting hydrogel forming polymer particles have a CCRC of about 50 g/g (absorption of 0.9% saline solution, as determined by methods known in the art and described herein); when 1.0 mol % (per mol AA) MBAA is used, the resulting hydrogel forming polymer particles have a CCRC of about 19 g/g; when 2.0 mol % (per mol AA) MBAA is used, the resulting hydrogel forming polymer particles have a CCRC of about 9 g/g.

All compounds were obtained by Aldrich Chemicals, and used without purification.

EXAMPLE 1.2

Process for the Preparation of Hydrogel Forming Polymers Useful Herein

To 300 g of glacial acrylic acid (AA), an appropriate amount of the core crosslinker (e.g., MethyleneBisAcrylAmide, MBAA) is added (see above) and allowed to dissolve at ambient temperature. A 2500 ml resin kettle (equipped with a four-necked glass cover closed with septa, suited for the introduction of a thermometer, syringe needles, and optionally a mechanical stirrer) is charged with this acrylic acid/crosslinker solution. Typically, a magnetic stirrer, capable of mixing the whole content, is added. An amount of water is calculated so that the total weight of all ingredients for the polymerization equals 1500 g (i.e., the concentration of AA is 20 w/w-%). 300 mg of the initiator ("V50" from Waco Chemicals) are dissolved in approx. 20 ml of this calculated amount of deionized water. Most of the water is added to the resin kettle, and the mixture is stirred until the monomer and water are well mixed. Then, the initiator solution is added together with any remaining water. The resin kettle is closed, and a pressure relief is provided, e.g., by puncturing two syringe needles through the septa. The solution is then spurged vigorously with argon via an 80 cm injection needle while stirring at ~300 RPM. Stirring is discontinued after ~8 minutes, while argon spurging is continued. The solution typically starts to gel after 12-20 minutes total. At this point, persistent bubbles form on the surface of the gel, and the argon injection needle is raised above the surface of the gel. Purging with argon is continued at a lowered flow rate. The temperature is monitored, typically it rises from 20° C. to 60-70° C. within an hour. Once the temperature drops below 60° C., the kettle is transferred into a circulation oven and kept at 60° C. for 15-18 hours.

After this time, the resin kettle is allowed to cool, and the resulting gel is removed into a flat glass dish. The gel is then broken or cut with scissors into small pieces (for example in pieces smaller than 2 mm max. dimension), and transferred into a 6 liter glass beaker. The amount of NaOH (50%) needed to neutralize 75% of the acid groups of the polymer is diluted with deionized water to 2.5 liters, and added quickly to the gel. The gel is stirred until all the liquid is absorbed; then, it is covered and transferred into a 60° C. oven and let equilibrate for 2 days.

After this time, the gel is allowed to cool, then divided up into 2 flat glass dishes, and transferred into a vacuum oven, where it is dried at 100° C./max. vacuum. Once the gel has reached a constant weight (usually 3 days), it is ground using a mechanical mill (e.g., IKA mill) and sieved to obtain hydrogel forming polymer particles of the required particle size, e.g., 150-800 µm. (At this point, key parameters of the hydrogel forming polymer as used herein may be determined).

The amount of MBAA may be adjusted, depending on what properties are required from the resulting polymers, e.g., when 0.01 mol % (per mol AA) MBAA is used, the resulting hydrogel forming polymer particles have a CCRC of about 90 g/g (absorption of 0.9% saline solution, as determined by methods known in the art and described herein); when 0.03 mol % (per mol AA) MBAA is used, the resulting hydrogel forming polymer particles have a CCRC of about 73 g/g; when 0.1 mol % (per mol AA) MBAA is used, the resulting hydrogel forming polymer particles have a CCRC of about 56 g/g; when 2.0 mol % (per mol AA) MBAA is used, the resulting hydrogel forming polymer particles have a CCRC of about 16 g/g; when 5.0 mol % (per mol AA) MBAA is used, the resulting hydrogel forming polymer particles have a CCRC of about 8 g/g. (All compounds were obtained by Aldrich Chemicals, and used w/o purification.)

EXAMPLE 1.3

Surface Cross-Linking Process Step

This example demonstrates surface crosslinking of hydrogel forming polymers prior to coating. A 150 ml glass beaker is equipped with a mechanical stirrer with a plastic blade, and charged with 4 g of a dry hydrogel forming polymer in particulate form. The mechanical stirrer is selected in such a way that a good fluidization of the polymers can be obtained at 300-500 RPM. A 50-200 µl syringe is charged with a 4% solution (w/w) of DENACOL (=EthyleneGlycolDiGlycidylEther=EGDGE) in 1,2-propanediol; another 300 µl syringe is charged with deionised water.

The hydrogel forming polymers are fluidized in the beaker at approx. 300 RPM, and the surface cross-linking agent is added within 30 seconds. Mixing is continued for a total of three minutes. While stirring is continued, 300 µl of water are then added within 3-5 seconds, and stirring is continued at 300-500 RPM for another 3 minutes. After this time, the mixture is transferred into a glass vial, sealed with aluminum foil, and let equilibrate for 1 hour. Then the vial is transferred to a 140° C. oven, and kept at this temperature for 120 minutes. After this time, the vial is allowed to cool down, the contents is removed, and the surface cross-linked hydrogel forming polymers are obtained. Any agglomerates may be carefully broken by gentle mechanical action. The resulting surface cross-linked hydrogel forming polymer particles may then be sieved to the desired particle size.

The following Examples Show Coating Processes that are Useful to Make the Water-Swellable Material of the Invention

EXAMPLE 2.1

Process of Providing Water Swellable Materials with Coated Hydrogel Forming Polymers by Directly Mixing Them into a Water Based Latex Dispersion.

The following is a preferred process for making the water-swellable material of the invention, involving swelling the hydrogel forming polymers prior to, or simultaneously with the coating step.

The amount of hydrogel forming polymers to be coated, coating level and water needed to swell the hydrogel forming polymers is chosen.

Then, the diluted dispersion of the coating agent is prepared, e.g., of the latex as described herein. This is done by mixing the commercial available elastomeric material and water and/or other liquid (if required) under stirring, for example in a glass beaker using magnetic stirrers at about 300 rpm for about 5 minutes. At all times, care needs to be taken that no film is formed on the surface of the dispersion. Typically for latex dispersions, the dispersion contains at the most 70% by weight of wet-extensible polymer.

In order to monitor the coating process better, a staining color might be added to the dispersion, for example New Fuchsin Red.

Then, a mechanical stirrer with a double cross Teflon blade is used and the dispersion is stirred such that a vortex can be seen, the hydrogel forming polymer (particles) are quickly added under continuous stirring. Once the hydrogel forming polymers start absorbing the water from the dispersion (typically after about 15 seconds), the mixture will start to gel and the vortex will eventually disappear. Then, when about all of the free liquid has been absorbed, the stirring is stopped and the resulting coated hydrogel forming polymers may be dried or post treated by any of the methods described herein.

EXAMPLE 2.2

Process of Providing Individually Coated Water Swellable Materials

An alternative preferred coating process of the invention is as follows:

The (solid, particulate) hydrogel forming polymers are placed on a surface that is preferably under an angle (3045 degrees).

The coating agent, in the form of a dispersion, is applied in drops, e.g., by use of a pipette or by spraying, onto the polymers. Hereby, no air bubbles should be formed.

Thus, a film is formed on the surface of the hydrogel forming polymers.

These coated hydrogel forming polymers are then dried, either at room temperature (20° C.), or for example at 40° C./80% humidity, for up to 2 days, or for example in an oven (if required, a vacuum oven) at a low temperature (up to 80° C.).

The coated water swellable material can then be cured as described below.

It may then also be formed into the desired form, e.g., particles.

EXAMPLE 2.3

Alternative Preferred Coating Process

In another preferred process, a dispersion of the hydrogel forming polymers is prepared first and the coating agent is added thereto.

For example, 200 grams of a hydrogel forming polymer (cross-linked polyacrylic acid based polymers, for example prepared by the method described above) is placed in a plastic beaker and n-heptane is added, until the heptane stands about 1-2 mm above the surface of the polymers in the beaker; this is typically about 100 g of n-heptane.

Using a household mixer (e.g., for whipping cream), the components are mixed at high speed. The coating agent, in the form of a water dispersion of a wet-extensible coating material, e.g., a latex dispersion as described above, is added to the beaker with the hydrogel forming polymers by use of for example a pipette. The mixture is continuously stirred, avoiding the formation of lumps.

The resulting material can be spread out over a surface as a thin layer (e.g., less than 1 cm) and allowed to air dry for at least 12 hours or in a (vacuum) oven (any temperature up to about 70C). The dried material may then additionally be cured by heating to 140° C. or 150° C. in a (vacuum) oven.

After cooling or subsequent steps, the resulting material may be mechanically reduced or sieved to the desired particle sizes.

EXAMPLE 2.4

Process of Providing Water-Swellable Material Comprising Coated Hydrogel Forming Polymers, in Accord with the Invention, Using a Fluidized Bed Wurster Coater The coating process step may also be done in a fluidized bed or Wurster coater.

For example, a GEA MP Micro coater (# 99194) may be used (supplied by Aeromatic-Fielder Ltd, School Lane, Chandlers Ford, Hampshire); or a Glatt GPCG-3 granulator-coater may be used (supplied by Glatt Ingenieurtechnik GmbH, Nordstrasse 12, 99427 Weimar, Germany). It may be desired that the coating equipment is pre-heated, for example to 70C, under air flow, for example for about 30 minutes.

Then, typically between 20 and 35 gram of hydrogel forming polymer is placed in the vessel (micro-coater case Makro; 2 kg).

The coating agent, preferably in fluid form (e.g., latex dispersion) is placed in a container on the stirring platform and stirred using a magnetic bar at low speed to prevent entrainment of air. The weight can be recorded.

The peristaltic pump is calibrated and then set to the desired flow rate (e.g., 0.1 g/minute) and the direction of flow of the coating agent is set forward. The desired inlet air flow and temperature are set (e.g., respectively 5 $m^3$/h, to reduce the risk of damage of the polymers; and, e.g., a temperature between 20 and 70° C.). Then, the atomising air supply and pump are started. (A higher speed may be used to advance the coating agent closer towards the inlet of the coater and then setting the correct speed for the experiment.)

The experiment is typically complete when stickiness prevents efficient fluidisation of the powder (between 20 and 60 minutes).

Then, the coating agent flow is stopped immediately and flow reversed. The weight of coating agent used in the experiment is recorded.

Optionally, the resulting coated hydrogel forming polymers may be dried within the coater, which also may aid to reduce particle surface stickiness (drying time typically between 20 and 60 minutes).

Then, the material inside the coater is weighed.

In general, the material may be returned to the coating vessel to continue the process, if required, e.g., if more than one coating agent is to be applied or to add a flow aid, e.g., 0.5-2% hydrophobic silica.

In order to visualise the coating process, or for aesthetic purposes, a colouring agent or dye solution may be added to the coating agent, for example New Fuchsin Red (0.25 g of New Fuchsin Red in 5 ml of 25 ml deionised water (15-25° C.), without entrainment of air bubbles). The dye solution can be added drop-wise to about 10 ml of the coating agent under stirring and this can then be stirred into the remaining coating agent (sufficient for up to 70 ml coating agent).

The following water-swellable materials were made by the process above, using a fluid bed coater or Wurster coater; in each case, 25 g of the uncoated hydrogel forming polymers, available as GV-A640 from Nippon Shokubai (lot 0019H 0000 ISA0331) was used and the specified amount of latex, at the specified weight-% solids concentration, was used.

After drying of the coated samples for 2 days as 35° C., each exemplified material was cured in vacuum at 140° C. for 2 hours.

| Example: | Latex: | Latex concentration (% w/w): | Amount of latex (g): |
|---|---|---|---|
| 1 | Hystretch V43 | 12.5% | 5.0 |
| 2 | Vinamul 330L | 50% | 2.5 |
| 3 | Vinamul Elite 21 | 50% | 2.5 |
| 4 | Vinamul Elite 21 | 50% | 5.5 |
| 5 | Vinamul Elite 21 | 25% | 3.0 |
| 6 | Vinamul Elite 21 | 12.5% | 4.5 |
| 7 | Vinamul Elite 21 | 25% | 3.0 |
| 8 | Vinamul Elite 21 | 50% | 3.5 |
| 9 | 75/25 PS:PB (experimental latex) | 20% | 3.0 |
| 10 | Rovene 4151 | 12.5% | 3.0 |
| 11 | Rovene 4151 | 25% | 2.0 |
| 12 | GenFlo 3075 | 50% | 2.5 |
| 13 | GenFlo 3088 | 50% | 1.0 |
| 14 | Suncryl CP-75 | 50% | 1.0 |

Hystretch is a trademark of Noveon Inc., 9911 Brecksville Road, Cleveland, Ohio 44141-3247.

Vinamul is a trademark of Vinamul Polymers, De Asselen Kuil 20, 6161 RD Geleen, NL.

Rovene is a trademark of Mallard Creek Polymers, 14700 Mallard Creek Road, Charlotte, NC 28262.

GenFlo and Suncryl are trademarks of Omnova Solutions Inc., 2990 Gilchrist Road, Akron, Ohio 44305-4418.

EXAMPLE 2.5

Preferred Subsequent Process Steps of Drying and Curing

The process of the invention may comprise a step whereby a solution, suspension or dispersion or solution is used, e.g., whereby the (coated) hydrogel forming polymers comprise a liquid (water) or whereby the coating agent is in the form of a dispersion, suspension or solution.

The following is a preferred process step of drying the coated hydrogel forming polymers of step b):

The coated hydrogel forming polymers or water-swellable material comprising a liquid, e.g., water, is placed on a surface, for example, it is spread out in a Pyrex glass pan in the form of a layer which is not more than about 1 cm thick. This is dried at about 70 Celsius for at least 12 hours.

If the amount of liquid present in the coated hydrogel forming polymers/material is known, then, by measuring the coated water-swellable material comprising said weight of liquid prior to drying and then subsequently after drying, one can determine the residual moisture in the resulting water-swellable material (coated hydrogel forming polymers) as known in the art. Typically, the resulting water-swellable material/coated hydrogel forming polymers will be dried to less than 5% (by weight of the material) moisture content.

The coated hydrogel forming polymers or material may subsequently be cured, for example in a vacuum oven at 140 Celsius for 2 hours.

For some type of coating agents, coated hydrogel forming polymers may potentially form agglomerates. Flow aids may be added prior to or during the coating step, or preferably during the drying and/or curing (annealing and/or cross-linking step), as known in the art, e.g., Aerosil 200, available from Degussa.

The above drying step may also be done by spreading the coated hydrogel forming polymers on a Teflon coated mesh in a very thin layer, e.g., less than 5 mm, such as to enable convection through the layer.

As alternative method, the coated hydrogel forming polymers that contain a liquid (water), may also be directly dried and cured in one step, e.g., placing the material in a vacuum oven at 140 Celsius for 2 hours.

EXAMPLE 2.6

Example: Method of Drying in Fluidized Bed

A Glatt coater as used in example 2.4 and other fluidized bed driers known in the art may also be used to dry the coated materials formed by step b) of the process. For example, the conditions of example 2.4 might be used, introducing the coated material (and thus using the Wurster coating equipment only for drying the coated material).

EXAMPLE 2.7

Method of Azeotropic Distillation and Drying

The wet, coated polymers may be dried or dewatered at low-temperature via azeotropic distillation from a suitable liquid, for example cyclohexane. For example, the coated polymers are transferred to a 2 liter resin kettle, equipped with a Trubore mechanical stirrer with Teflon blade and digital stirring motor, immersion thermometer, and Barrett type moisture receiver with graduated sidearm and water-cooled condenser. Approximately one liter of cyclohexane is added to the resin kettle. While stirring, a heating mantle is used to raise the temperature of the stirred cyclohexane/gel system to reflux. Reflux is continued until the temperature of the system approaches the boiling point of cyclohexane (approximately 80° C.) and only minimal additional quantity of water is delivered to the sidearm. The system is cooled and then filtered to obtain the dewatered or dried coated hydrogel forming polymers, which may be further dried overnight under vacuum at ambient temperature (20 C).

Test Methods Used Herein:

(Unless specified otherwise, each test to obtain a value parameter herein is done 3 times to obtain an average of 3 values.)

Methods to Determine Whether an Elastomeric Coating is Non-Breaking

The following method is used to determine whether the elastomeric coating of hydrogel forming polymers comprised in the water-swellable material of the invention is non breaking. This is done by first staining and then swelling the water-swellable material and thus the coated hydrogel forming polymers therein, and then investigating the elastomeric coating on the swollen hydrogel forming polymers, by the following method.

A) Staining of the Water-Swellable Material of the Invention with Toluidine Blue in 0.9% NaCl.

Staining Solution (20 PPM Toluidine Blue O in 0.9% NaCl):

20 mg Toluidine Blue 0 [CAS: 540-23-8] is dissolved in 250 ml 0.9% (w/w) NaCl solution. The mixture is placed into an ultrasonic bath for 1 hour, filtered through a paper filter, and filled up to 1000 ml with 0.9% NaCl solution.

Staining Procedure:

A sample of 30-50 mg of the water-swellable material is placed in screw cap glass vial, and 30 ml of the above staining solution is added. The vial is closed, and the material is allowed to swell and equilibrate for 18 hours at 20-25° C. during gentle agitation (e.g., gentle swirling or slow rolling of the vial on a roller mill).

B) Alternative Oxidative Staining Method with $MnO_4^-$— solution:

An alternative visualization of the elastomer coating material can, e.g., be achieved by an oxidative staining with $MnO_4$.

Hereby, the water-swellable material of the invention is first swollen in a 0.9% NaCl solution:

A sample of 30-50 mg of the water-swellable material of the invention is placed into a 40 ml screw cap glass vial, and 30 ml of 0.9% NaCl solution in water are added. The vial closed and the material is allowed to swell and equilibrate at 20-25° C. for 18 hours under gentle agitation via occasional gentle shaking or rolling on a roller mill.

Oxidative Staining Procedure:

Then, the swollen material is stained as follows:

20-25 mg $KMnO_4$ are dissolved in 100 ml 0.9% (w/w) NaCl solution.

Excess liquid is removed from the swollen water-swellable material (e.g., by letting it drip off) and 30 ml of the $KMnO_4$ solution is added, while gently swirling of the solution for a few minutes. This gentle swirling is repeated at intervals of 15-20 minutes. After 60-90 minutes, the staining solution is removed, and the AGM is washed several times with 0.9% NaCl solution. As some $MnO_4$ will bleed from the swollen particles, washings may have to be repeated in intervals of 10-15 minutes. The staining is complete when the supernatant does not pick up a noticeable purple color any more.

C) Alternative Oxidative Staining Method Using $OsO_4$ (or $RuO_4$)

The water-swellable material is swollen as in B above.

Then, a few drops of a solution of $OSO_4$ in water (4% w/w) are then added to the swollen material, and gently swirled for 30 min-1 day. Then, the staining solution is removed, and replaced by 0.9% saline. After 1 hour, the solution is discarded, and the saline solution is added one more time to remove excess oxidant.

Similarly, $RuO_4$, freshly prepared from $RuO_2$ or $RuCl_3$ (following procedures described in for example "Polymer Microscopy", Linda C. Sawyer, David T. Grubb, Chapman and Hall, New York, ISBN 0 412 25710 6), may be used for staining, especially for elastomeric coatings rich in aromatic moieties (e.g., styrene-rich elastomeric coatings).

Assessment of the Percentage Non-Breaking Coating

For microscopy assessment, a swollen, stained sample as prepared by any of the methods above is weighed and then transferred into white porcelain dishes, and covered with the solution in which they were prepared (or placed into 1 cm glass or quartz cuvettes with a stopper in contact with this solution).

Separately, un-coated hydrogel forming polymers may also be submitted to the respective staining method and this assessment for comparison.

A stereomicroscope (e.g., Olympus Stereomicroscope SZH10 (7-70×), equipped with a circular illumination (e.g., Intralux UX 6000-1, Volpi AG, CH 8952 Schlieren, Switzerland), and optionally a camera (e.g., Olympus ColorView 12), may be used for evaluation of the swollen, stained, coated AGM particles.

As described above, with this equipment the particles with a non-breaking coating can be distinguished, visually, from the material without non-breaking coating. Then, the particles with a non-breaking coating are separated from those without non-breaking coating and the two fractions are weighed; the weight of the two fractions together is the total weight of the sample; then, the weight percentage (compared to the total weight) of the particles with the non-breaking coating can be calculated.

To obtain a meaningful percentage of particles with a non-breaking coating, the total of solids (e.g., particles) observed should be at least 100.

Determination of Cylinder Centrifuge Retention Capacity of Water-Swellable Materials This test serves to measure the saline-water-solution retention capacity of the water-swellable material or hydrogel forming polymers used herein, when the water-containing material (polymer) are submitted to centrifuge forces (and it is an indication of the maintenance of the absorption capacity of the polymers in use, when also various forces are applied to the material).

First, a saline-water solution is prepared as follows: 18.00 g of sodium chloride is weighed and added into a two liter volumetric flask, which is then filled to volume with 2 liter deionised water under stirring until all sodium chloride is dissolved.

A pan with a minimum 5 cm depth, and large enough to hold four centrifuge cylinders is filled with part of the saline solution, such that up to a level of 40 mm (±3 mm).

Each sample is tested in a separate cylinder and each cylinder to be used is thus weighed before any sample is placed in it, with an accuracy of 0.01 g. The cylinders have a very fine mesh on the bottom, to allow fluid to leave the cylinder.

For each measurement, a duplicate test is done at the same time; so two samples are always prepared as follows:

1.0 g of the water-swellable material (or hydrogel forming polymers) which is to be tested is weighed, with an accuracy of 0.005 g (this is the 'Sample'), and then the sample is transferred to an empty, weighed cylinder. (This is repeated for the replica.)

Directly after transferring the sample to a cylinder, the filled cylinder is placed into the pan with the saline solution (Cylinders should not be placed against each other or against the wall of the pan.).

After 15 min (±30 s), the cylinder is removed from the pan, and the saline solution is allowed to drain off the cylinder, then, the cylinder is re-placed in the pan for another 15 min. After the total of 2×15 minutes=30 minutes immersion time, the cylinder is taken from the solution and excess water is allowed to run off the cylinder and then, the cylinder with the sample is placed in the cylinder stands inside a centrifuge, such that the two replicate samples are in opposite positions.

The centrifuge used may be any centrifuge equipped to fit the cylinder and cylinder stand into a centrifuge cup that catches the emerging liquid from the cylinder and capable of delivering a centrifugal acceleration of 250 G (±5 G) applied to a mass placed on the bottom of the cylinder stand (e.g., 1300 rpm for a internal diameter of 264 mm). A suitable centrifuge is Heraeus Megafuge 1.0 VWR # 5211560. The centrifuge is set to obtain a 250G centrifugal acceleration. For a Heraeus Megafuge 1.0, with a rotor diameter of 264 mm, the setting of the centrifuge is 1300 rpm.

The samples are centrifuged for 3 minutes at 250G (±10 s).

The cylinders are removed from the centrifuge and weighed to the nearest 0.01 g.

For each sample (i), the cylinder centrifuge retention capacity Wi, expressed as grams of saline-water-solution absorbed per gram of water-swellable material (or hydrogel forming polymer) is calculated as follows:

$$w_i = \frac{m_{CS} - (m_{Cb} + m_S)}{m_S} \left[\frac{g}{g}\right]$$

where:
$m_{CS}$: is the mass of the cylinder with sample after centrifugation [g]
$m_{Cb}$: is the mass of the dry cylinder without sample [g]
$m_S$: is the mass of the sample without saline solution [g]

Then, the average of the two $W_i$ values for the sample and its replica is calculated (to the nearest 0.01 g/g) and this is the CCRC as referred to herein.

Method to Determine the Free Swell Rate of Water Swellable Materials Herein

This method serves to determine the swell rate of the water-swellable materials herein in a 0.9% saline solution, without stirring or confining pressure. The amount of time taken to absorb a certain amount of fluid is recorded and this is reported in gram of fluid (0.9% saline) absorbed per gram of water-swellable material per second, e.g., g/g/sec.

The saline solution is prepared by adding 9.0 gram of NaCl into 1000 ml distilled, deionized water, and this is stirred until all NaCl is dissolved. 1.0 gram of the sample material is weighed (to an accuracy of 0.0001 g) and placed evenly over the bottom of a 25 ml beaker; then 20 ml of the saline solution (also at 23C) is added quickly to the beaker with the sample and the timer is started.

When the last part of the undisturbed fluid surface meets the swelling sample, e.g. judged by the light reflection from the fluid surface, the time $t_s$ is recorded.

The test is repeated twice, to obtain 3 values.

The Free Swell Rate is then calculated per sample and this can be averaged to obtain the Free swell rate, as referred herein.

Determination of the Coating Caliper and Coating Caliper Uniformity

The coatings on the hydrogel forming polymers of the water-swellable materials herein can typically be investigated by standard scanning electron microscopy, preferably environmental scanning electron microscopy (ESEM) as known to those skilled in the art. In the following method the ESEM evaluation may be used to determine the average coating caliper and the coating caliper uniformity of the coated hydrogel forming polymers via cross-section of the materials.

Equipment Model: ESEM XL 30 FEG (Field Emission Gun)

ESEM setting: high vacuum mode with gold covered samples to obtain also images at low magnification (35×) and ESEM dry mode with LFD (large Field Detector which detects 80% Gaseous Secondary Electrons+20% Secondary Electrons) and bullet without PLA (Pressure Limiting Aperture) to obtain images of the latex shells as they are (no gold coverage required).

Filament Tension: 3 KV in high vacuum mode and 12 KV in ESEM dry mode.

Pressure in Chamber on the ESEM dry mode: from 0.3 Torr to 1 Torr on gelatinous samples and from 0.8 to 1 Torr for other samples.

Samples of coated water-swellable material or hydrogel forming polymers or of uncoated polymers can be observed after about 1 hour at ambient conditions (20C, 80% relative humidity) using the standard ESEM conditions/equipment.

Then, the same samples can be observed in high vacuum mode.

Then the samples of coated hydrogel forming polymers can be cut via a cross-sectional cut with a Teflon blade (Teflon blades are available from the AGAR scientific catalogue (ASSING) with reference code T5332), and observed again under vacuum mode.

The coatings have different morphology than the uncoated hydrogel forming polymers and the coatings are clearly visible in the ESEM images, in particular when observing the cross-sectional views.

The average coating caliper is determined then by analyzing at least 5 particles of the hydrogel forming polymer, coated with a non-breaking coating, and determining 5 average calipers, an average per particle (by analyzing the cross-section of each particle and measuring the caliper of the coating in at least 3 different areas) and taking then the average of these 5 average calipers.

The uniformity of the coating is determined by determining the minimum and maximum caliper of the coating via ESEM of the cross-sectional cuts of at least 5 different particles of hydrogel forming polymers, coated with a non-breaking coating, and determining the average (over 5) minimum and average maximum caliper and the ratio thereof.

If the coating is not clearly visible in ESEM, then other staining techniques known to the skilled in the art that are specific for the coating applied may be used such as enhancing the contrast with osmiumtetraoxide, potassium permanganate and the like, e.g. prior to using the ESEM method.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A water-swellable material that comprises hydrogel forming polymers coated by a coating formed from a coating agent comprising an elastomeric polymeric material, whereby said coating is present at a level of at least 1% by weight of the water-swellable material, and wherein the water swellable material has a CCRC of at least 10 g/g and wherein, for at least a part of the coated hydrogel forming polymers, said coating is non-breaking, when the water-swellable material is swollen to equilibrium in 0.9% saline solution and wherein said part of the coated hydrogel forming polymers that has a non-breaking coating of an elastomeric polymeric material is at least 60% by weight of the material having a coating with an elastomeric, polymeric material.

2. A water-swellable material according to claim 1, wherein the coating has an average thickness of at least 5 µm.

3. A water-swellable material according to claim 1, wherein the coating has an average thickness of at least 10 µm.

4. The water-swellable material according to claim 1, wherein the coating covers at least about 80% of the surface of the hydrogel forming polymer.

5. The water-swellabie material according to claim 1, wherein the coating is completely continuous.

6. The water-swellable material according to claim 1, wherein the coating is completely connected.

7. The water-swellable material according to claim 1, wherein the coating completely circumscribes the hydrogel forming polymer.

8. The water-swellable material according to claim 1, wherein the hydrogel forming polymer is in particulate form.

9. The water-swellable material according to claim 8, wherein the hydrogel forming polymer has a mass median particle size of from about 10 µm to about 1 mm.

10. A water-swellable material that comprises hydrogel forming polymers, coated by a coating formed from a coating agent comprising an elastomeric polymeric material, whereby said coating is present at a level of at least 1% by weight of the water-swellable material, and wherein the water swellable material has a CCRC of at least 10 g/g and wherein, for at least a part of the coated hydrogel forming polymers, said coating is non-breaking, when the water-swellable material is swollen to equilibrium in 0.9% saline solution, and wherein the coating has an average thickness of at least 1 µm.

11. A water-swellable material that comprises hydrogel forming polymers, coated by a coating formed from a coating agent comprising a polyurethane, whereby said coating is present at a level of at least 1% by weight of the water-swellable material, and wherein the water swellable material has a CCRC of at least 10 g/g and wherein, for at least a part of the coated hydrogel forming polymers, said coating is non-breaking, when the water-swellable material is swollen to equilibrium in 0.9% saline solution.

* * * * *

UNITED STATES PATENT AND TRADEMARK OFFICE
CERTIFICATE OF CORRECTION

| | |
|---|---|
| PATENT NO. | : 7,270,881 B2 |
| APPLICATION NO. | : 10/912002 |
| DATED | : September 18, 2007 |
| INVENTOR(S) | : Mattias Schmidt et al. |

It is certified that error appears in the above-identified patent and that said Letters Patent is hereby corrected as shown below:

Column 5

Line 43, delete "10 m" and insert --10μm--.

Line 43, delete "1200m" and insert --1200μm--.

Column 11

Line 7, delete "B-Alanin" and insert --β-Alanin--.

Line 14, delete "Camitin" and insert --Carnitin--.

Column 12

Line 29, delete "LAPONUEs™" and insert --LAPONITEs--.

Line 41, delete "la" and insert --lattice charge--.

Column 14

Line 20, in the formula, insert a parenthesis --(-- in front of the first CH.

Column 23

Line 36, delete "3045" and insert --30-45--.

Signed and Sealed this

Twenty-eighth Day of October, 2008

JON W. DUDAS
*Director of the United States Patent and Trademark Office*